United States Patent
Joosten

(10) Patent No.: US 7,911,606 B2
(45) Date of Patent: Mar. 22, 2011

(54) METHOD FOR OPERATING AN OPTICAL EMISSION SPECTROMETER

(75) Inventor: Heinz-Gerd Joosten, Kranenburg (DE)

(73) Assignee: Spectro Analytical Instruments GmbH, Kleve (DE)

( * ) Notice: Subject to any disclaimer, the term of this patent is extended or adjusted under 35 U.S.C. 154(b) by 621 days.

(21) Appl. No.: 11/814,051

(22) PCT Filed: Nov. 4, 2005

(86) PCT No.: PCT/EP2005/011799
§ 371 (c)(1),
(2), (4) Date: Apr. 9, 2008

(87) PCT Pub. No.: WO2006/074725
PCT Pub. Date: Jul. 20, 2006

(65) Prior Publication Data
US 2008/0198377 A1    Aug. 21, 2008

(30) Foreign Application Priority Data
Jan. 17, 2005   (DE) .................. 10 2005 002 292

(51) Int. Cl.
*G01J 3/30*    (2006.01)
(52) U.S. Cl. .................. 356/313; 250/458.1; 250/461.2; 356/301; 356/318; 356/417
(58) Field of Classification Search .................. 356/301, 356/313, 317, 318, 417; 250/458.1–461.2
See application file for complete search history.

(56) References Cited

U.S. PATENT DOCUMENTS

| | | | |
|---|---|---|---|
| 5,141,314 A | 8/1992 | Belmore et al. | |
| 2005/0140974 A1* | 6/2005 | Irie et al. | 356/313 |
| 2005/0174583 A1* | 8/2005 | Chalmers et al. | 356/630 |

FOREIGN PATENT DOCUMENTS

| | | |
|---|---|---|
| DE | 4106627 | 5/1992 |
| DE | 19753348 | 6/1999 |
| DE | 10152679 | 4/2003 |
| EP | 0396291 | 11/1990 |
| EP | 1035410 | 9/2000 |
| EP | 1355145 | 10/2003 |
| EP | 1486772 | 12/2004 |

OTHER PUBLICATIONS

International Search Report issued in corresponding International Application No. PCT/EP2005/011799 on Feb. 22, 2006.
Written Opinion issued in corresponding International Application No. PCT/EP2005/011799 on Jul. 24, 2007.

* cited by examiner

*Primary Examiner* — Gregory J Toatley
*Assistant Examiner* — Iyabo S Alli
(74) *Attorney, Agent, or Firm* — Connolly Bove Lodge & Hutz LLP

(57) ABSTRACT

The invention relates to a method for the spectral analysis of metal samples with the following steps:
a. Recording of a spectrum of an unknown sample with a number of preset excitation parameters,
b. Comparison of the spectrum with stored spectra of a number of control samples,
c. Determination of the control sample with the best concordance of spectra,
d. Setting of the excitation parameters, which are stored for the best and closest control sample determined in step c,
e. Recording of the spectrum of the unknown sample with the excitation parameters set in step d,
f. Calculation of the intensity ratios of the analysis lines stored for the control sample and the internal standards of the spectrum recorded in step e.

13 Claims, 11 Drawing Sheets

METHOD FOR OPERATING AN OPTICAL EMISSION SPECTROMETER

CROSS-REFERENCE TO RELATED APPLICATIONS

This application is a U.S. National Stage Application based on PCT/EP2005/011799, filed on Nov. 4, 2005, which draws priority from German Patent Application No. 102005002292.8, filed on Jan. 17, 2005.

BACKGROUND

The present invention relates to a method for the operation of an optical emission spectrometer.

Emission spectrometers with spark and/or arc excitation are used in the multi-element routine analytics of metals. FIG. 1 shows the general prior art on the basis of a diagrammatic representation of the structure of such systems. The stand (1) allows for the mounting of a sample (2) at a distance of 0.5 to 5 mm from a counter-electrode (3). The excitation generator (4) firstly creates a high voltage pulse, which ionizes the atmosphere between the sample surface and the counter-electrode (air or inert gas) and so renders it of low resistance (low-Ohmic).

With the arc generator, a direct current of strength 1 A to 10 A is then fed via the low-resistance spark path; this arc is sustained for a period from 0.5 s to 10 s. Arcs of this nature are mostly operated in an air atmosphere.

Instead of one single long pulse, a spark generator generates short pulses of a duration of 50 µs to 2 ms with a sequence frequency of between 50 Hz and 800 Hz. A new ignition pulse is required before each individual spark. A thermal plasma is formed with temperatures of between 4,000 K and 20,000 K, in which free atoms and ions are excited for the emission of a line spectrum. The emitted light is conducted into an optical system (5), on the focal curve (6) of which the spectral lines are sharply formed. The spark excitation takes place as a rule in an argon atmosphere.

At the present time there are two conventional methods for measuring the spectral lines sharply imaged on the focal curve.

1. The first type of spectrometer system is shown in FIG. 2, which also represents the prior art. The light impinges through a source slit (7) onto a concave grating (8). A spectrum occurs as a plurality of wavelength-dependent diffraction patterns of the source slit. The spectral lines of interest are masked out with exit slits (9) and their intensity is measured by means of photomultiplier tubes (10).

2. The second conventional form of spectrometer design according to the prior art is shown in diagrammatic form in FIG. 3. With this design, too, the light falls through a source slit (7) onto the grating (8). However, instead of an individual exit slit, multi-channel sensors (11) are arranged here along the focal curve (6). These multi-channel sensors consist of a linear arranged field of photo-sensitive sensor elements, referred to as pixels. In this design, a simultaneous absorption of complete spectral ranges is possible.

The conventional calibration of the spectrometer systems now takes place in such a way that the totality of the materials to be analyzed with the system are subdivided into material groups of similar chemical composition. If it is intended, for example, that a spectrometer system should measure all materials which consist predominantly of iron, such groups are low-alloyed steels, cast irons, manganese steels, chrome steels, and chrome-nickel steels.

For each of these material groups combinations of analyte lines and lines of the basic element are known (iron in the example referred to), which are particularly well-suited for setting up a calibration function. The lines of the basic element (referred to as the internal standards) serve to compensate changes in the plasma. They are individually selected to suit each analysis line. The calibration function of an analysis line is determined first by a set of standard samples being measured for a given group of materials. Next, the intensity ratio for each sample (quotient of the measured value of the analysis line divided by the measured value of the internal standard pertaining to it) is applied against the concentration ratio (concentration of the analyte divided by the concentration of the basic element). Finally, a polynomial is determined over these value pairs (each value pair is the tuple (concentration ratio, intensity ratio)) by means of regression calculation with which the sum of the square deviations between the polynomial and the sample concentration ratio is minimal. In the simplest case, the polynomial which is found is the calibration function which is sought. It is often necessary, however, for the influences of third elements to be taken into account in the regression calculation. The performance of this calculation is described, for example, in Slickers [K. A. Slickers: Automatic Atom-Emission Spectral Analysis, Brohische Universitatsdruckerei, Giessen, 1992]. The standard deviation of the deviations between calibration and sample concentration ratio is designated as scatter residual (abbreviated to SR). Suitable calibration functions are characterised by a low scatter residue.

If precise analyses are to be carried out of metals from material groups with sharply varying contents of alloy elements, the electrical spark is the method of choice. Combinations of analysis lines and internal standards can be found of which the scatter residue is perceptibly lower than that of the best line pairs known with arc excitation. It is also to be pointed out that with arc excitation and calibrations of material groups with sharply varying element contents no line pairs can be found and the variation coefficient of the intensity ratios is, as a rule, unsatisfactory. It often lies at between 10% and 50%, in comparison with the typical 3-10% with arc excitation and alloy groups with low concentration variations, and 0.1-3% for spark calibrations.

The good accuracy and high precision of the spark excitation are obtained at the expense of certain disadvantages:

The use of Ar flushing with typical flushing rates of 2 l/min during the measurement requires that a voluminous and heavy pressure cylinder be carried with the system, which renders portable systems impractical.

The spark excitation requires a clean ground flat surface. With heavily dirt-contaminated or oxidised surfaces, there will be no or only irregular material decomposition.

A spark measurement typically lasts for 15 s as opposed to typically 3 s with arcs.

The spark opening must be sealed against the surrounding atmosphere during the measurement. The penetration of air impairs the measurement. Spark apertures of 4 to 20 mm are usual. It follows from this that only samples can be measured which are provided with a flat surface of the given size.

Excitation with an arc is therefore substantially easier to carry out, in particular with portable spectrometers.

BRIEF SUMMARY OF EMBODIMENTS OF THE INVENTION

The object of the present invention is therefore to provide a method and device which will substantially improve the analytical performance capacity, in particular with the application of spark excitation.

This object may be accomplished by means of a method comprised as follows:

a. Recording of a spectrum of an unknown sample with a number of preset excitation parameters; b. Comparison of the spectrum with stored spectra of a number of control samples; c. Determination of the control sample with the best concordance of spectra; d. Setting of the excitation parameters, which are stored for the best and closest control sample determined in step c; e. Recording of the spectrum of the unknown sample with the excitation parameters set in step d; f. Calculation of the intensity ratios of the analysis lines stored for the control sample and the internal standards of the spectrum recorded in step e.

This object may further be accomplished by means of a device comprised as follows: an excitation source, which operates on the principle of electrical excitation; at least one optical system for the splitting of the optical emission in spectral lines; a number of location resolving detectors; a control device for the sequence of the spectral analysis; characterised in that a memory is provided for a plurality of control sample data records, wherein one control sample data record comprises at least one part of a control sample spectrum and excitation parameters provided for this control sample, and in that the control unit is designated to set the excitation parameters automatically.

DETAILED DESCRIPTION OF EMBODIMENTS OF THE INVENTION

Figure 1:
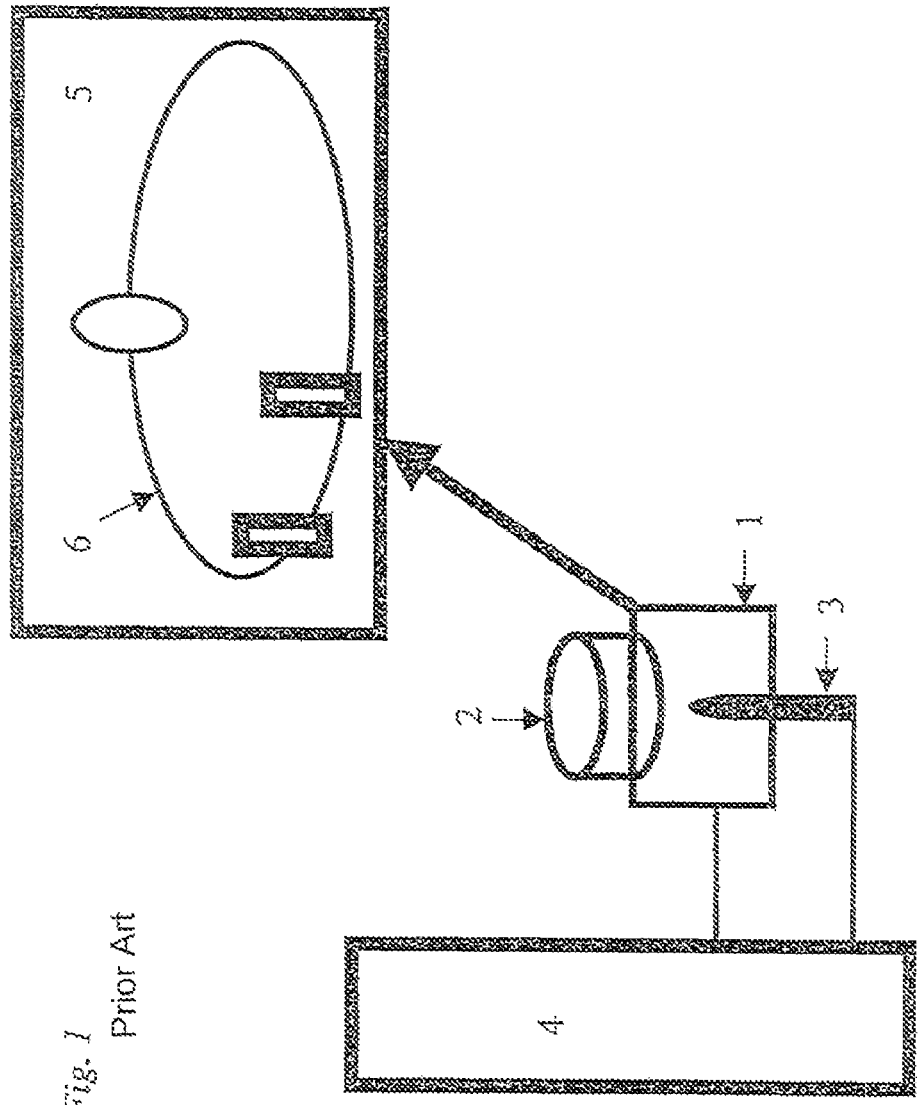
FIG. 1 shows a general structure of a prior-art system.
Figure 2:
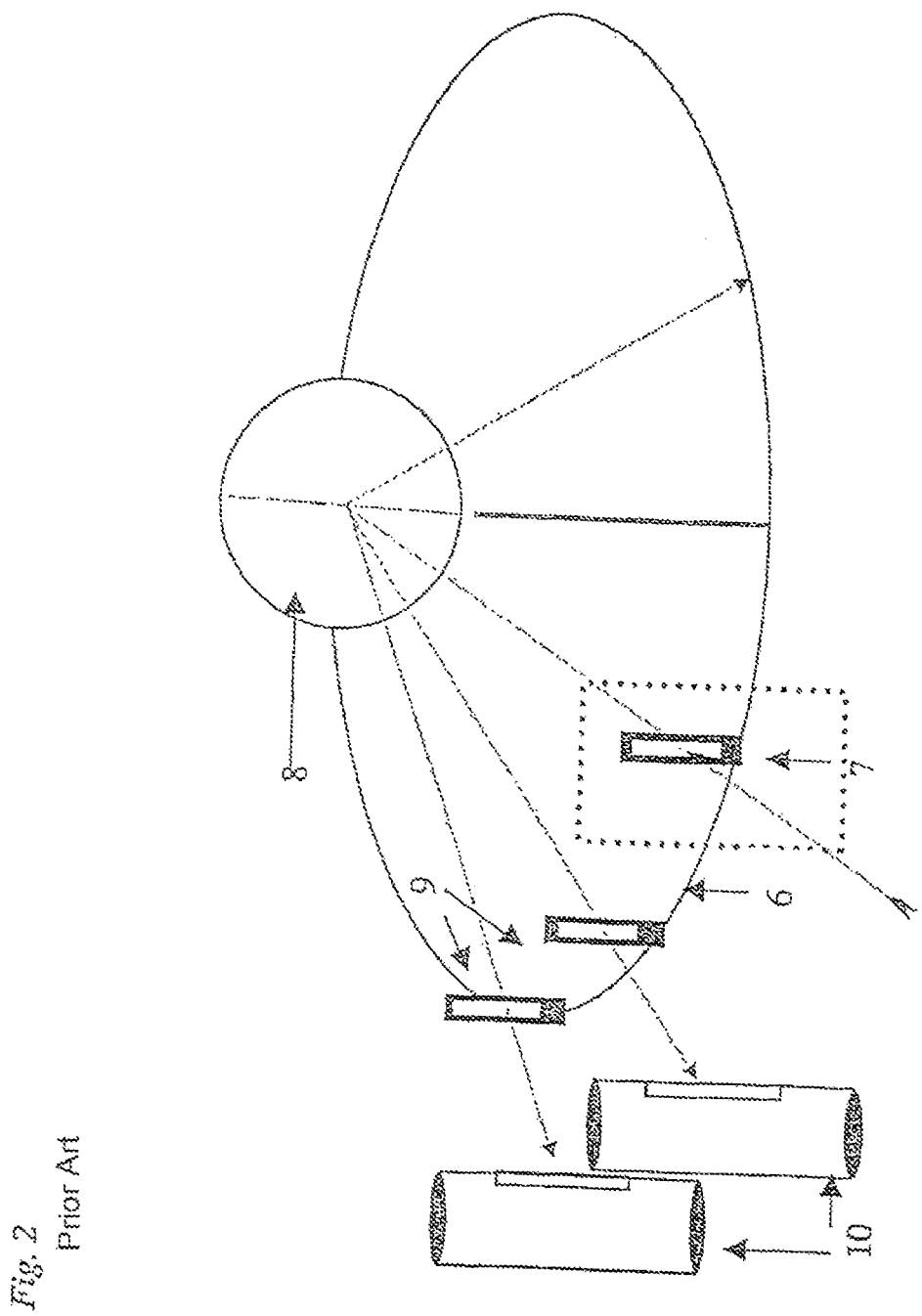
FIG. 2 shows a prior-art spectrometer system.
Figure 3:
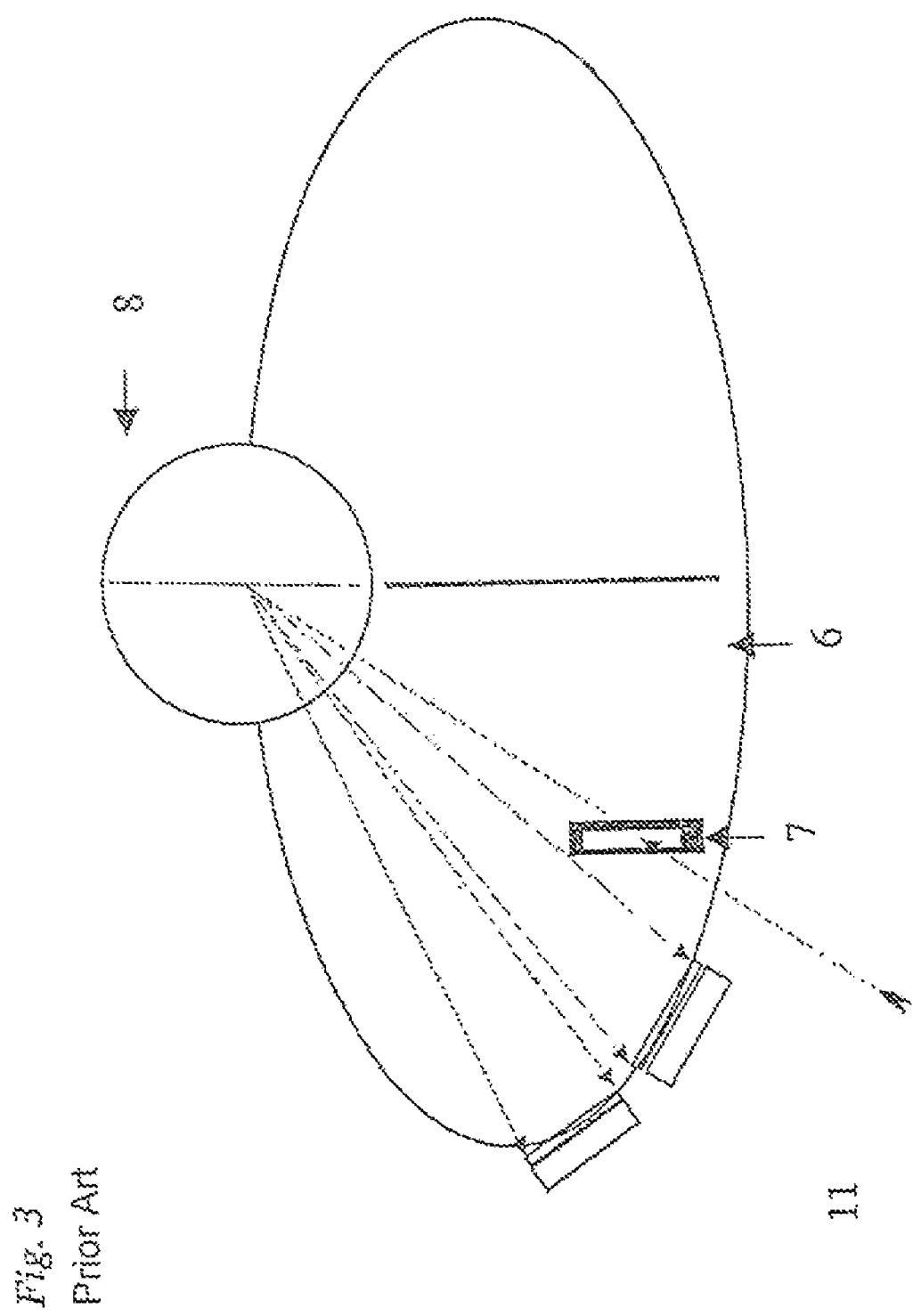
FIG. 3 shows a prior-art spectrometer system.

The resolution of the task of improving the analytical performance capacity is rendered possible with the method by means of the following method steps:

a. Recording of a spectrum of an unknown sample with a number of pre-set excitation parameters,
b. Comparison of the spectrum with stored spectra of a number of control samples,
c. Determination of the control sample with the best concordance of spectra.
d. Setting of the excitation parameters which are stored for the best and closest control sample determined in step c.,
e. Recording of the spectrum of the unknown sample with the excitation parameters set in step d.,
f. Calculation of the intensity ratios of the analysis lines stored for the control sample and the internal standards of the spectrum recorded in step e.

The initially fully unknown sample can therefore initially be allocated to a control sample and then precisely analysed with suitable parameters in a second step. With the use of arc excitation, it is therefore possible to achieve close to the precision of a spectral analysis with spark excitation.

The method can in principle also be used for electrical spark generation. In this case, the precision in the determination of many elements can be improved by more than a factor of two and the analysis correctness by more than a factor of three.

The method can be used for spectrometer systems of the second design type, in other words, for such spectrometers as are equipped with multichannel sensors for full spectrum recording.

An additional advantage of the method is the method for full spectrum recalibration described in the German Patent Application DE 101 52 679 A1. With the aid of this method, spectra of any desired device of a manufacturing range can be converted into the spectrum of a reference device. Accordingly, it is possible to get identical spectra for a given sample and for any system after application of the conversion.

Preferably, with arc excitation a fixed arc current pre-adjusted in step a. of 1.5 to 2.8 Amperes is used. Particularly good results can be achieved if in step b. the number of deviations is determined between the lines in the sample spectrum and the control sample spectrum for each control sample, and in step c. that control sample is selected with the lowest number of deviations. During the evaluation it is preferred if the precise concentration ratios for each alloy element El are determined in accordance with the formula:

$$KV_{El}=KV_{Leit}+E*(1-Int_{El}/Int_{Leit}).$$

or an equivalent method. The attaining of the concentration $K_{El}$ for each element El of a total of n elements from the concentration ratios is effected preferably in accordance with the formula according to Equation 2, shown below. By storing the line selection as a function of the control sample, it is possible for the concentration calculation to be restricted to those elements which are to be anticipated in alloys of the control sample class found and which are capable of analysis there.

The ease of use is further improved if the output of the element concentrations is effected in a sequence stored with the control sample and if the element concentrations are transferred for further processing, in particular for a routine for alloy identification.

Because with the device according to the invention a memory is provided for a large number of control sample data records, wherein a control sample data record comprises at least a part of a control sample spectrum and excitation parameters provided for this control sample, and because the control unit is designed to set the excitation parameters automatically, a measurement can be carried out with particular precision.

In particular, the excitation source can be an arc excitation source, the excitation parameters can comprise at least the arc current, and/or the control sample data records can comprise information regarding spectral lines suitable for the spectral analysis of each individual control sample.

The control unit can be designed for a fully automatic analysis, such that in a first analysis it sets an excitation parameter independent of a control sample in order to carry out a first spectral analysis, compares the result with the control sample data records and then sets the excitation parameters which are stored for the closest control sample.

In order to provide motivation for the concept of the method, it is firstly necessary to consider the basic physical differences between arcs and sparks.

The spark starts when the argon atmosphere between the electrode tip and the sample surface is ionized by a high-voltage pulse. The spark path extremely rapidly turns from a very large to a very small resistance. The source now sets the current which is specified by the current curve which has been specified. In this situation a plasma channel forms, which is some thousands of degrees in temperature. Because of the high temperatures still more (positively charged) argon ions are formed, which are accelerated in the direction of the sample surface and there strike metal atoms from the surface. The metal atoms form a hot vapour. They take on the impingement energy of the argon ions and impact with hot particles from the plasma channel. The high temperatures lead to the metal atoms emitting the spectrum which is characteristic of them. The metal atoms are partially ionized and emit ion spectra. However, before metal ions can be accelerated in their turn in a number worth mentioning back in the direction of the sample surface, the conductive phase of the spark is passed. The ignition phase of the arc runs identically to that of the spark. The only exception is that nitrogen and oxygen ions knock the metal atoms off the sample surface. Things then proceed differently, however. The arc, typically conducts current for several seconds (e.g. 3), while the current flow with one individual spark lasts about 100 microseconds. In other words, the arc has about 300,000 times the length of an individual spark. The material decomposition process described in the discussion of the spark therefore develops further. The metal atoms are ionized and accelerated back to the sample. They therefore contribute to their own decomposition. Their contribution rapidly exceeds that of the gas ions, since these are much lighter than the metal ions (and also much lighter than argon ions). The further decomposition process is now dependent on which elements the sample contains. If it contains elements with high atomic weight, the heavier ions which are derived have a high kinetic energy. There is a tendency for more material to be decomposed than if the sample were to consist primarily of light elements. If more than 4% of light elements (Al, Si, C, B) are present, they additionally press the plasma apart and ensure that no more melt forms at the foot point of the arc. In this situation, particularly little material is decomposed. The atom lines disappear almost entirely because the whole of the decomposed material is ionized in order to maintain the current flow impressed from the source.

Third elements can therefore lead to completely different decomposition behaviour. Due to this, the correlation between line intensities and concentrations with the use of arc excitation becomes understandable.

It is, on the other hand, plausible and demonstrable by experiment that samples of similar composition also have a similar decomposition behaviour. This is also the reason why the arc calibration is entirely usable for low-alloyed steel: In this case the sample is mainly bombarded with iron ions and light elements likewise do not occur in high content quantities.

Figure 4:
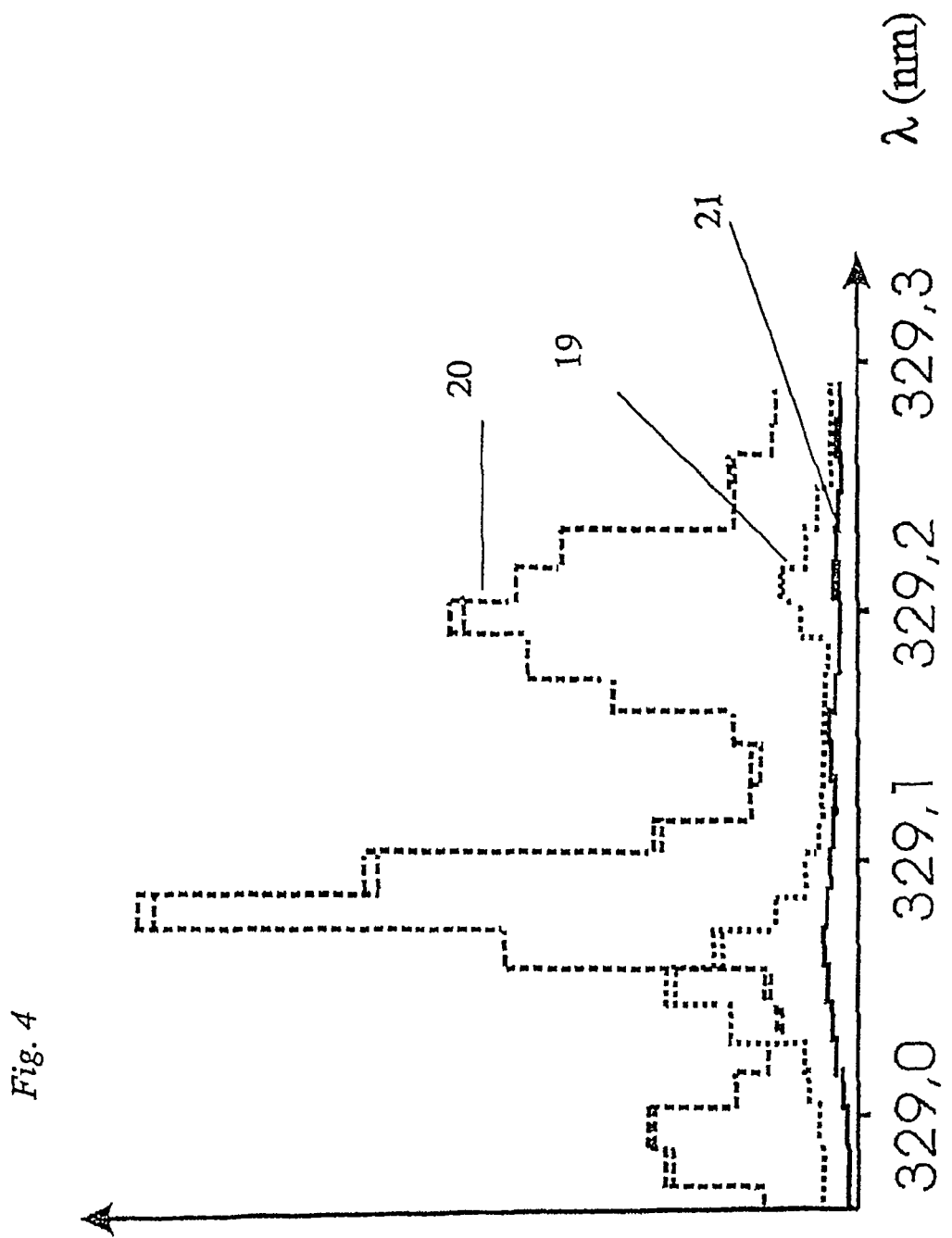
FIG. 4 shows measurements of spectra of alloys.

It is known to spectroscope users that every alloy has a characteristic spectrum, which only vary rarely runs the risk of being confused with the spectrum of a sample from another alloy. FIG. 4 makes the situation clear. In this situation, three different nickel samples of the alloys 2,4375 (19), 2,4634 (20) and Ni 200 (21) were each measured twice. The spectra of a double measurement are close to one another and differ clearly from all other measurements. The risk of confusion is impossible. It may be seen that the allocation is successful, although here only a spectrum extract of about 0.3 mm is represented. Usually, however, in metal spectrometers with multi-channel detectors a spectral range of between 200 nm and 600 nm is available.

The arrangement is now pursued, according to an embodiment of the invention, of the palette of metals to be analyzed being subdivided into groups in such a way that metals of one group show a similar decomposition behaviour. Measurements show that this is then the case if in all the metals of a group the same combination of alloy elements is present and the contents of the alloy elements do not vary too sharply. If two metals in at least one alloy element differ from one another by more than 5% in absolute terms or more than 100% relatively, they are as a rule to be allocated to different groups. The non-alloyed steels C60 and St37 belong, according to this logic, to the same alloy group, as do CuSn6 and CuSn8. The aluminium alloys 226 (AlSi9Cu3) and 230 (AlSi12), however, fall into two different groups, because 226 contains 3% Cu, but alloy 230 is copper-free. An alloy is now selected from each group, and from these a sample procured which is as homogenous as possible and analyzed. These samples are designated hereinafter as control samples. About 200 control samples are required in order to cover a large proportion of the conventional alloys.

To carry out the calibration method according to an embodiment of the invention, the spectrum of each control sample is now firstly measured and stored. The measurement takes place with parameters which, with regard to excitability, represent a usable compromise for a large proportion of the control samples. In this situation, a current of 1.8-2.2 A and a measurement duration of approx. 1.5 s have proved to be advantageous. For the analysis of an unknown sample, firstly its spectrum is measured, always with the same parameters as were also used at the recording of the control sample spectra. Next, the spectrum obtained in this way is compared with all the control sample spectra, and the qualitatively best-suited control sample is determined. To determine the best-suited control sample the spectrum of each control sample is then compared with that of the unknown sample and the number of deviation points determined. A deviation point is present if:

The spectrum of the unknown sample has a spectral line at the point concerned, but the control sample spectrum does not, or the spectrum of the control sample has a spectral line at the point concerned, but the spectrum of the unknown sample does not.

In addition, it is a good approach to count a point in the spectrum as a deviation if two spectra have a spectral line at the same point but the intensities of the lines differ substantially (if, for example, the quotient of the intensities of the more substantial spectral line to the weaker spectral line is greater than three). In a real spectrum acquired with a spectrometer of infinite resolution, overlaps of closely adjacent spectral lines occur. For the purpose of identification of the best control sample, such overlapped lines are treated as one single one.

A weak spectral line can disappear in noise in the spectrum of the unknown sample but be present in the spectrum of the control sample due to a slightly higher content, or vice-versa. It is a good approach to count only unambiguous deviations. These are such as arise if a line in a spectrum is raised so far above the noise level that in the comparison spectrum the corresponding line would in any event have to be visible even in lower concentration, but nevertheless is not demonstrable. Details of the method are based on the sensor hardware which is to be specifically used. This has a determinant influence on the dynamic range available. A version of the algorithm worked out in detail is also to be found hereinafter within the framework of the description of a specific embodiment of the invention. The optimum control sample, in an embodiment of the invention, is that of which the spectrum has a minimal number of deviation points in comparison with the unknown sample. As has already been noted in the preamble, it is a good approach, before using the method according to the invention to carry out a full spectrum recalibration as in the Patent Application DE 101 52 679 A1. With an increasing time interval to the last full spectrum recalibration carried out, it may occur that too small a deviation arises between the pixel positions of the maximum of a spectral line in the spectrum of the control sample and the pixel positions of the maximum of a spectral line in the spectrum of the unknown sample. Generally, these are pixel fractions. These deviations become greater if the spectrometer optics are subjected to temperature or pressure changes. In this context, a predominant position deviation $\Delta P$ is found over broad spectral ranges (approximately constant for all spectral lines $\lambda$).

This position deviation is determined as follows: If the line maximum of a spectral line $\lambda$ was located immediately after the spectra recalibration at the pixel position $P_\lambda$ and is currently located at pixel position $P'_\lambda$, then $\Delta P_\lambda = P_\lambda - P'_\lambda$. $\Delta P_\lambda$ stands for the arithmetical mean of $\Delta P_\lambda$ for all spectral lines $\lambda$. Experiments show that it is sufficient for $\Delta P$ to be estimated with a subset of spectral lines. In this context, the subset used should contain a sufficiently great number of lines (>20), which are adequately densely distributed (at least one line per 20 nm). If $\Delta P$ exceeds a predetermined limit, then the suitability of the system for analysis is questionable. According to an embodiment of the invention, it is a good approach to consider a spectral line in the spectrum of the unknown sample and in the spectrum of the control sample as equivalent, even if their peak maxima have a small position difference $\Delta P$, provided that a specified maximum limit $P_{max}$ is not exceeded. $\Delta P_{max}$ is in this context measured as somewhat greater than the maximum profile displacement to be tolerated over the temperature and pressure operating range of the spectrometer optics.

If the interval $[\Delta P_{max} - \Delta P_{max}]$ is subdivided into K classes (e.g. 20), a frequency distribution of the deviations can be formed. The median M of this frequency distribution is the predominant position deviation according to an embodiment of the invention. As mentioned earlier, this is a usable estimation for $\Delta P_1$ provided that, in a comparison of the spectra of the unknown sample and of the control sample, a sufficient number of corresponding line pairs has been found and these also cover the spectrum with sufficient density.

If the deviations $\Delta P_1$ belonging to the individual line pairs are considered, in the ideal case all the deviations are equal and lie in the same class of frequency distribution. In practice, however, noise influences lead to a scattering over adjacent classes. It is therefore a good approach, as a plausibility check, to check the interquartile interval I of the frequency distribution. If I is small in comparison with |M| (e.g. I<|M|*0.2), a significantly predominant deviation has indeed been determined.

If M exceeds a predetermined limit $G_{ReKal}$ to be determined by experiment, the analysis reliability of the system is no longer guaranteed, and according to an embodiment of the invention, a new full spectrum recalibration is required. Within the framework of the full spectrum recalibration according to Patent Application DE 101 52 679 A1, for each physical pixel Px a pixel offset Opx is determined, which indicates by how many pixels the measured spectrum must be displaced in order to Come into congruence with the spectrum of the reference device. These pixel offsets Op are used in order to displace the measured spectra in such a way that each line appears at the same place as with the reference device. As long as the displacement $\Delta P_\nu$ determined now remains below $G_{ReKal}$, according to an embodiment of the invention, the recalibration function can be updated by the operation Op:=Op+$\Delta P_\nu$. However, a variable TotalOffset is to be used, which is set to zero after each full spectrum recalibration. During the updating of the pixel offset, the TotalOffset is also to be updated: TotalOffset:=TotalOffset+$\Delta P_\nu$. As soon as TotalOffset>$G_{ReKal}$, the offsets have changed by more than $G_{ReKal}$ and a new recalibration is required. It will be observed that the drift correction described functions with any desired samples of unknown composition. At this point of the method it is known to which material group the unknown sample belongs. This is already more than can in general be achieved with the conventional calibration method with the use of arc excitation. In comparison with the conventional calibration method and the use of the spark under argon, there is indeed the advantage that no material group-specific measuring method needs to be pre-selected, but the spark delivers precise values for each analysis element and not only a 5% absolute or 100% relatively broad content range.

Figure 5:
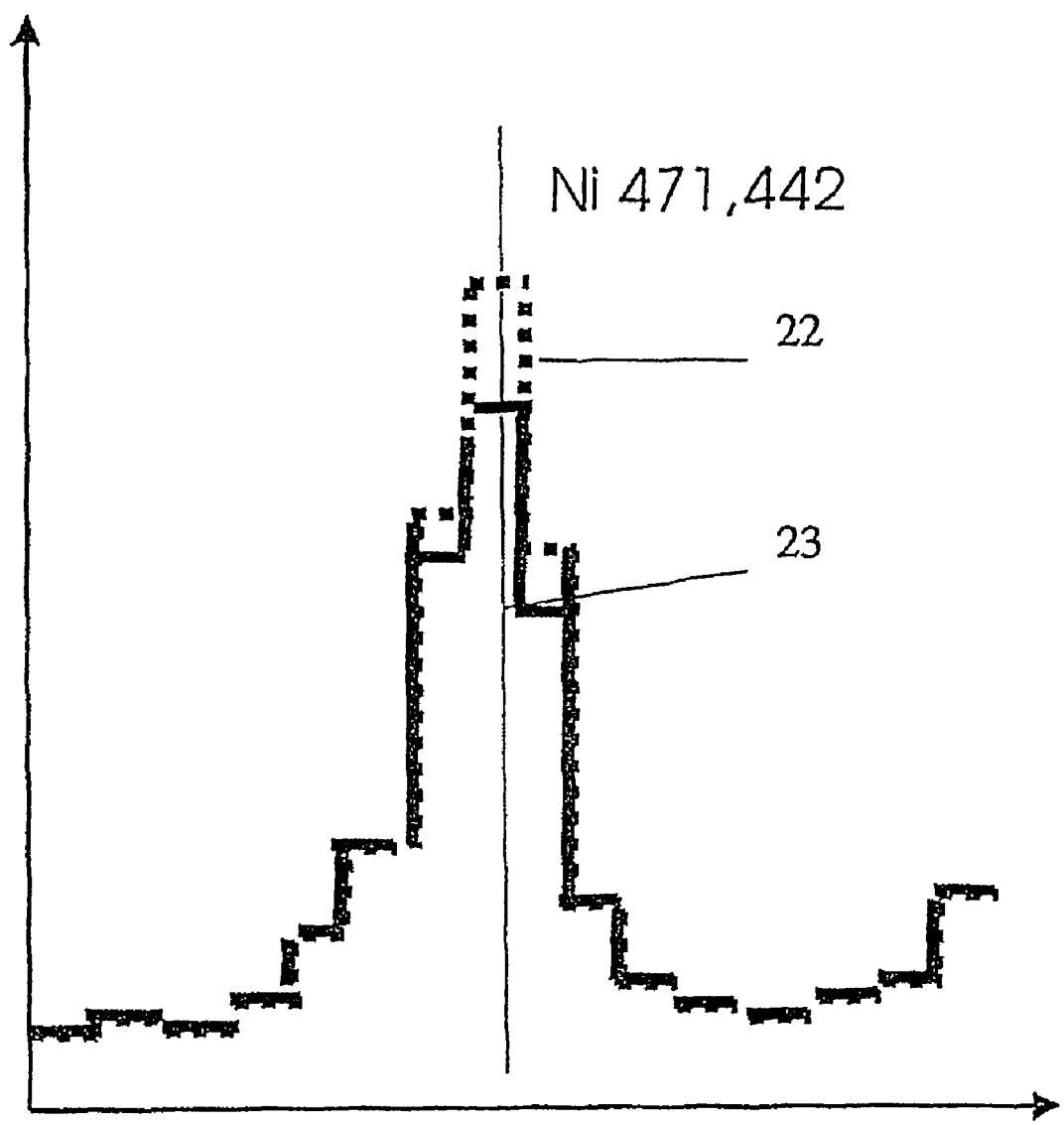
FIG. 5 shows further measurements.

Within one control sample group, the element contents can be determined by interpolation. FIG. 5 illustrates the principle. A nickel line at 471.4 nm is represented. The control sample (stainless steel, quality 1,4401) has a nickel content of 10.1%. The unknown sample is likewise a stainless steel (quality 1,4404) with a 12.1% nickel content. The signal from the unknown sample (22), at 471.4 nm, is about 15% higher than that of the control sample (23). If it is now known that for the nickel line a 471.4 nm intensity deviation per percent is to be anticipated (from the control sample intensity) with a concentration deviation of 0.75% (relative to the control sample concentration), the concentration of the unknown sample can be calculated.

A difficulty arises with this, however. The variation coefficient of the individual measurements can, as already mentioned, amount to up to 50% according to material, current and line. This means that within one measurement series consisting of ten measurements relative deviations between the highest and lowest value of up to 150% are to be anticipated. Accordingly, no decision must be made as to whether a higher intensity in the spectrum of the unknown sample really has its cause in a higher element content or is of a purely coincidental nature.

Figure 6:
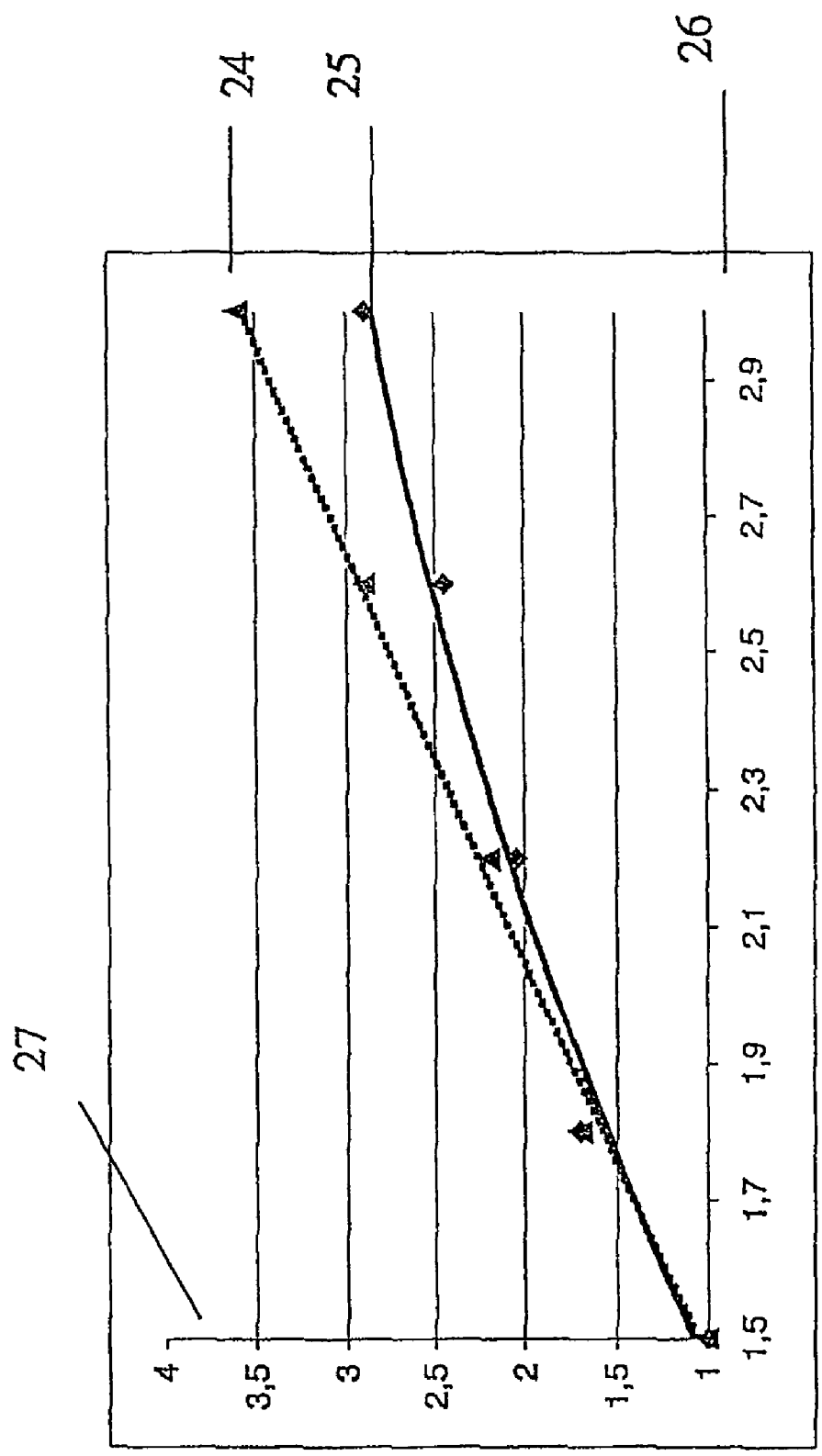
FIG. 6 shows how current intensities may change.

In order to be able to provide motivation for the solution of this problem described in the invention, consideration must first be given to some special features of the electric arc. The current is the most important arc excitation parameter. It has a great influence on the average arc temperature and therefore on the material decomposition and excitation (hereinafter reference is made to arc temperature although 'the' arc temperature does not exist as a scalar value. Different temperatures pertain at different points of the plasma. This spatial distribution also changes in the course of a measurement). In order to make clear the influence of the arc current on the signal intensities, a sample of the material 2,4955 (16% Fe, 50% Ni, 27% Cr) with currents of between 1.5 and 3 A were measured and the intensity changes associated with these on the two nickel lines of two adjacent nickel lines Ni 1 388.9 nm and Ni 1 397.2 nm were determined. FIG. 6 shows the intensity changes normed to the mean intensity values of the line concerned at 1.5 A (intensity change of the Ni line 388.97 nm (24) to the intensity change of the Ni line 397.22 nm (25)).

It is striking that the intensities with arc current changes vary to differing degrees on the two lines although the two lines are atom lines with similar excitation potential (3.39 and 3.54 eV respectively).

For the excitation, the value of the plasma temperature is decisive. It is only possible to make a rough check on the temperature of the arc by way of the arc current, however. Even with entirely constant current, temperature fluctuations occur which cannot be influenced from outside. To make this clear, the measurement points in FIG. 6 may be considered.

Figure 7:
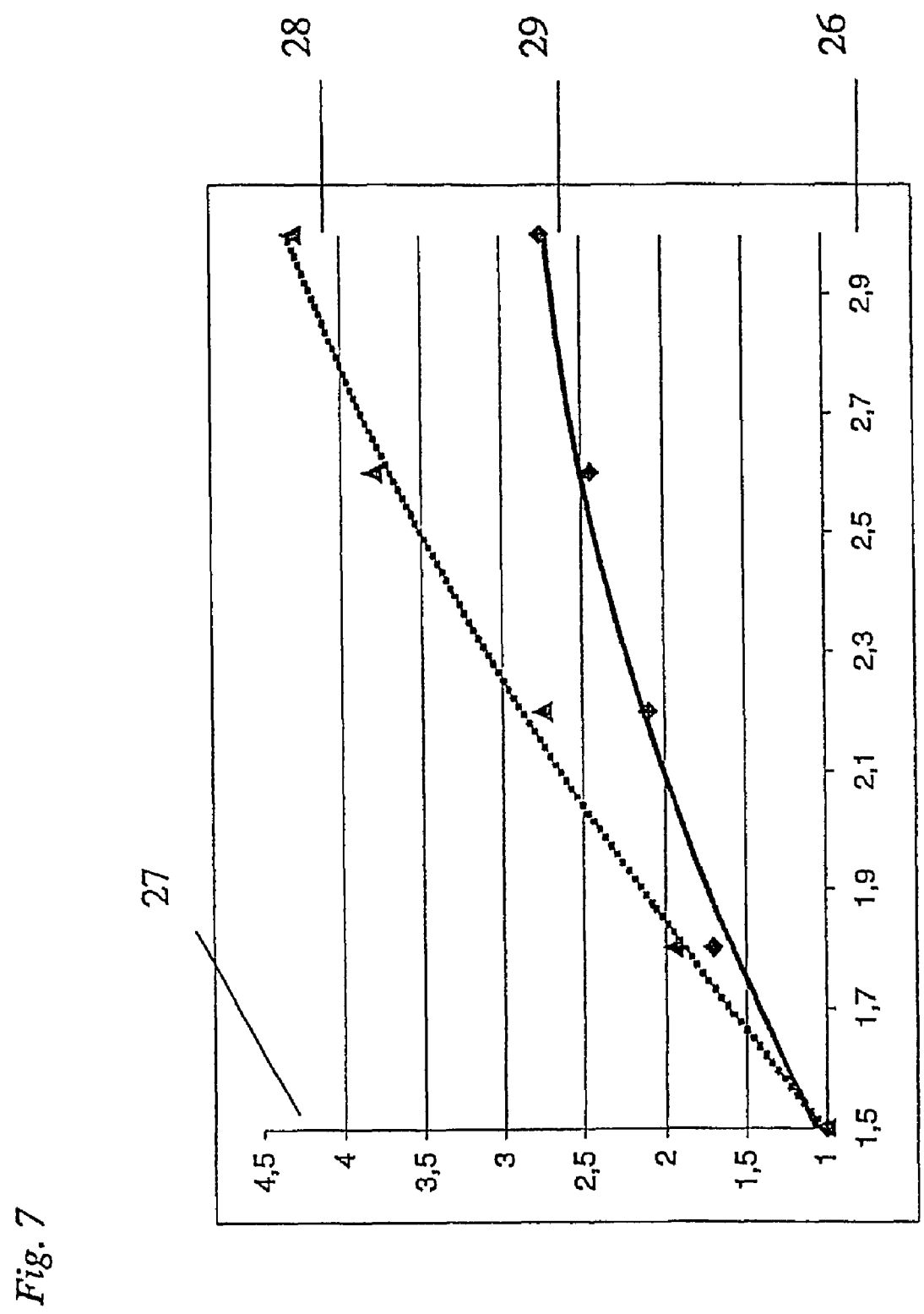
FIG. 7 shows a plot of current dependencies.
Figure 8:
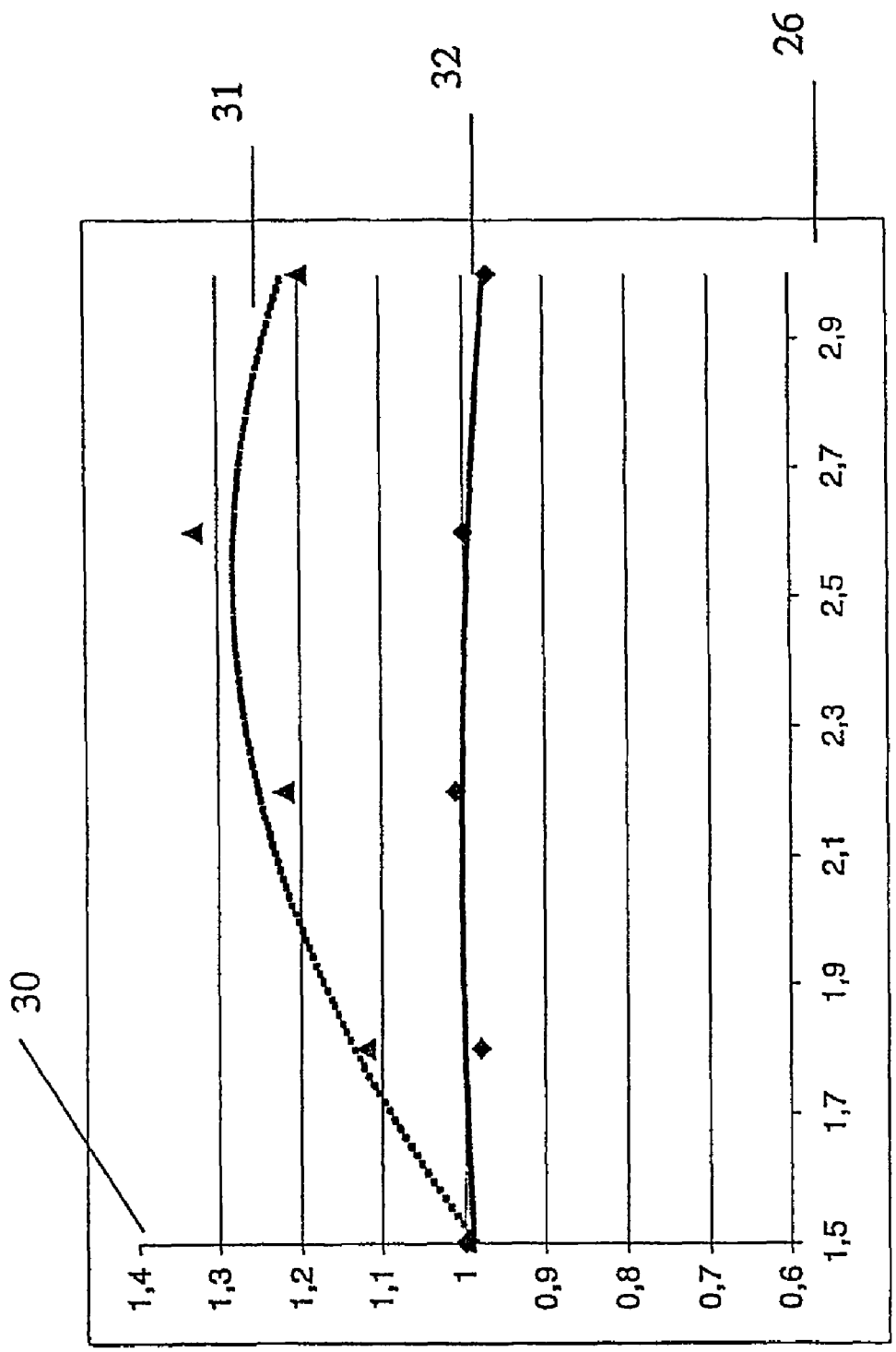
FIG. 8 shows plots representing effects of current changes on intensity ratios.
Figure 9:
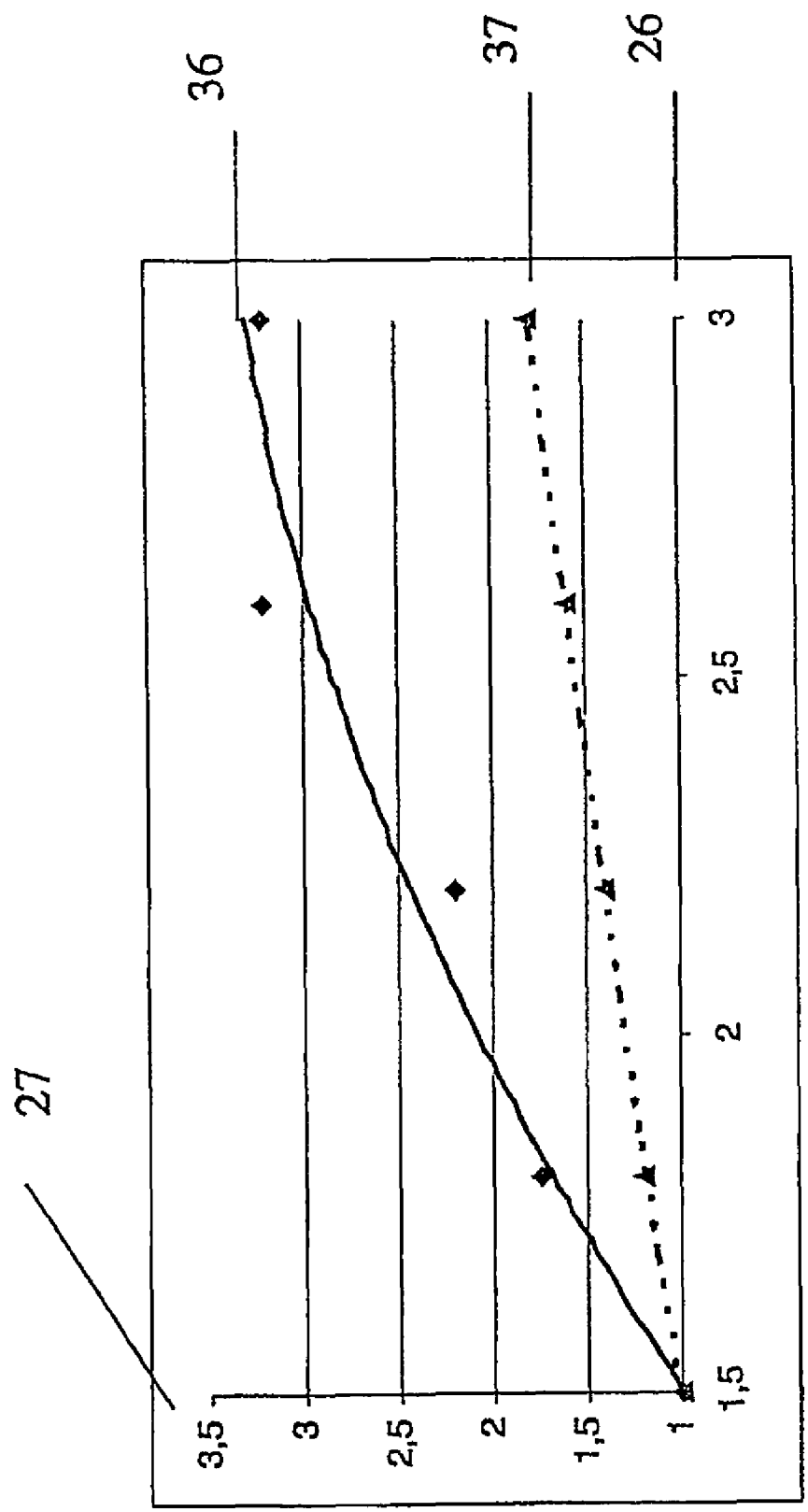
FIG. 9 shows another intensity change plot.

Each of the points is a mean value from three individual values. For the arc flow 3 A and the line Ni 1 388.9 nm, the individual measurement 1 gave 3.31 times the mean intensities at 1.5 A, the measurement 2 3.53 times and the measurement 3 3.98 times. On the current axis this would correspond to a current variation of between 2.8 and 3.4 A. The arc current, however, was kept constant during all three measurements to within a few mA. It is to be suspected that turbulence at the plasma edge leads to these uncontrollable temperature fluctuations. In FIG. 7, the current dependency is shown for the two Cr lines, Cr 1 385.4 nm and Cr 1397.1 nm. Here too, despite the same line type and very similar excitation energy (5.92 and 5.82 eV respectively), there is a sharply differing intensity increase at a current increase from 1.5 to 3 A. The example alloy 2,4955 is an Ni-based alloy with Cr as one of the main alloy elements. From the example lines, line pairs can be formed with in each case a Cr line as the analyte line and an Ni line as the internal standard. If it now proves possible to find a current range for which the rise in the intensity curves is approximately the same at the Cr and Ni line, the reproducibility of the intensity ratio will be good. Chance temperature fluctuations do not then result in any fluctuation of the intensity ratio. FIG. 8 shows for the two line pairs Cr 397.13/Ni 397.22 (32) and Cr 385.42/Ni 388.97 (31) the effects of current changes on the intensity ratios. The first line pair harmonises well and current fluctuations between 1.5 and 2.3 A and corresponding temperature fluctuations have scarcely any effect on the intensity ratios. The second line pair, by contrast, is perceptibly worse. In this case, a current rise from 1.5 A to 2.3 A has the effect of increasing the intensity ratio by about 25%. The intensity increase with the current rise, however, is not dependent on the lines alone but also on the material being measured, as FIG. 8 shows. In this case, instead of the alloy 2,4955 nickel 200 (Ni>99.2%) was measured. The intensity of the Ni 388.97 nm increases with current doubling only by 80%. With the current doubled on the material 2,4955, the intensities had increased almost fourfold. The picture is the opposite with the Ni 397.22 nm. Here, the intensities with nickel 200 rise by the factor of 3.2; on the 2,4955 a rise by only a factor of 2.8 was recorded. Mention has already been made of the influence of the material composition on the decomposition mechanism.

The examples show that (by contrast with the spark OES under argon) no line pairs exist in the arc which provide good reproducibility for a broad current range and widely differing materials. For individual alloys and narrow current ranges, however, line pairs are to be found of which the intensity ratio reproduces well.

For narrowly circumscribed material groups with a specified arc current, however, line pairs can be found which allow for measurements with a precision which are entirely capable of being compared with those of the spark OES. This is shown by the following example for Co in Waspaloy, measured with an arc current of 1.5 A:

| Mean variation coefficient, % | Variation coefficient (3 * every 10 measurements) | Analysis line/ line type excitation energy | Int. Std./ line type/ excitation energy | % intensity ratio rise at 1% concentration rise (E) |
|---|---|---|---|---|
| 0.67 | 0.7 0.7 0.6 | Co 3385.22\| | Ni 3467.5\|3.73 | 0.86 |
| 0.70 | 0.8 0.8 0.5 | Co 3442.93\|3.78 | Ni 3467.5\|3.73 | 0.50 |
| 0.76 | 1.0 0.7 0.6 | Co 4771.11\|5.73 | Ni 4971.35\|7.03 | 0.57 |
| 0.77 | 0.8 0.5 1.0 | Co 3334.14\|4.15 | Ni 3688.42\|3.63 | 0.82 |
| 0.80 | 1.0 0.8 0.6 | Co 3417.16\|4.21 | Ni 3467.5\|3.73 | 0.27 |
| 0.83 | 0.9 0.8 0.8 | Co 3086.78\|4.24 | Ni 3467.5\|3.73 | 0.64 |
| 0.83 | 1.0 0.9 0.6 | Co 4813.48\|5.44 5.79 | Ni 3688.42\|3.63 | 0.79 |
| 0.84 | 0.9 0.9 0.7 | Co 4813.48\|5.44 5.79 | Ni 4592.53\|6.24 | 0.98 |
| 0.88 | 1.0 0.9 0.7 | Co 4813.48\|5.44 5.79 | Ni 4935.83\|6.45 | 0.98 |
| 0.91 | 0.9 0.6 1.3 | Co 3611.7\|5.75 | Ni 3688.42\|3.63 | 0.71 |

The mean variation coefficients listed relate to intensity ratios, not concentrations. As a result, a sensitivity factor E was also determined, which indicates how sharply the intensity increases at a concentration increase by 1%. The reproducibility for concentrations is obtained by dividing the variation coefficients of the intensity ratios by the sensitivity factors pertaining to them. It is possible to examine all line pairs to the degree of precision to be produced, for every conventional alloy, every rational current value and every relevant alloy element in the material concerned. The best material-specific line pairs found in this way are required in order to carry out in full the method for the spectrum-based concentration calculation.

Once the best-suited control sample has been found, it is determined in accordance with an embodiment of the invention what choice of line pairs is optimum for all materials similar to the control sample. The arc generator is adjusted in accordance with an embodiment of the invention to the optimum current for the line pairs stored for the control sample which has been found. Because the unknown sample corresponds qualitatively to the control sample, these parameters are also suitable for it. A second measurement period is then carried out. From the spectra acquired in this way, the concentration ratios of the line pairs are determined by interpolation and converted with the 100% calculation usual with spark emissions (see, for example [Slickers]) into concentrations. The sequence with which the elements appear on the screen and to which the analyst is accustomed is dependent on the alloy. It is therefore recommended that the element sequence for each control sample should be stored and the calculated concentrations be issued accordingly.

By storing the line selection as a function of the control sample, it is now possible for the concentration calculation to be restricted to those elements which are to be expected in alloys of the control sample class found and which are capable of analysis there.

This is a particularly advantageous performance feature of the method. For example, the element Ta in steels is actually only of interest for Cr/Ni alloys. In the case of tool steels, it is advantageous to dispense with determining this element because Ta is never contained in these steels but, due to line overlaps at the point where the line is located, a high intensity is nevertheless measured. Accordingly, with a dimensioning of the line distortions correct for stainless steels, a content of approximately 0.5% Ta is nevertheless calculated. If a user or downstream software accepts the value indicated unchecked, an incorrect material analysis will be produced. There are very many examples of this type; one such is Pd in a Ti base. In this case, Pd only occurs in non-alloyed Ti and can only be determined there. If 1% Pd is incorrectly shown, this can lead to substantial errors in the value determination of Ti scraps. The feature, that due to the element selection being dependent on the alloy group, only lines capable of analysis are actually used for the determination of the contents, is therefore particularly advantageous for the material analysis. The numerical values cited above as examples relate in this context to optics with a resolution capacity of 0.1 nm and to specific tool steels and Ti alloys.

To summarise, the method sequence is as follows:

1: The unknown sample is measured with a fixed arc current

2: The closest control sample is determined with the spectra determined in this way 3: The optimum current suitable for this control sample is switched on 4: The unknown sample is measured with the arc current optimum for it 6: The intensities of the analysis lines stored for the control sample and internal standards are drawn from the spectrum derived in this way 7: The intensity ratios are formed 8: The precise concentration ratios are formed by the following calculation being carried out for each alloy element El:

$$KV_{El} = KV_{Leit} + E^*(1 - Int_{El}/Int_{Leit}) \quad \text{(Equation 1)}$$

where:

$KV_{El,U}$: Concentration ratio of the unknown sample for element El $KV_{El,Leit}$: Concentration ratio of the control sample for element El E: Sensitivity factor (see above)

$Int_{El,U}$: Intensity ratio for the line pair used for the element El, measured on the unknown sample $Int_{El,Leit}$ Intensity ratio for line pair used for the element El, measured on the control sample, stored in the control sample record 9: From the concentration ratios, for each element El of a total of n elements the concentration $K_{El}$ is calculated in accordance with the following equation:

$$K_{El} = \frac{KV_{El}}{\left(100 + \sum_{i=1}^{n} KV_{i,U}\right)} \quad \text{(Equation 2)}$$

10: The element concentrations are output in a sequence stored with the control sample or conducted to a further processing stage (e.g. to a routine for the alloy identification).

A specific embodiment of the invention is described in greater detail hereinafter. In this context, consideration is given in particular to the identification of the control sample (step 2 in the sequence plan referred to above). The other steps always run in the same way, regardless of the sensor type used, and have already been adequately described by the comments made above.

In outlining the algorithm for control sample identification, a comparison of all positions of resolved spectral lines of two spectra was carded out. The spectrum of the unknown sample is stored in a field Mes[ ]. Mes[Px] designates the intensity of the pixel Px. Superimpositions of non-resolved spectral lines are regarded as one unit. Accordingly, instead of lines or superimposed line groups, reference is made hereinafter to peaks.

The following questions must first be clarified:

How can it be determined whether a peak is located inside a pixel interval [Px;Px+δ]?

How can the exact position of a recognised peak be determined?

Recognition of a Peak

If a peak is present in the spectral range of a pixel, the peak intensity must be a local maximum of Mes, and the following must therefore apply:

$$Mes[Px] > Mes[Px-1] \wedge Mes[Px] > Mes[Px+1] \quad \text{(Equation 3)}$$

The intensities of the pixels left and right of Px must therefore be smaller than the intensity with Px. In order to be able to assess this local maximum as a peak, it must be certain that the increased intensity at Px does indeed derive from an increased radiation intensity of the spectrum at the pixel Px (compared with the intensity in the spectrum at pixels Px−1 and Px+1). This is not always the case, however, if more intensities were measured at Px than at Px−1 and Px+1. Real spectrometer systems are subject to shortcomings. For samples which consist of elements with low-line spectra, there are sensor pixel ranges onto which no radiation or only background radiation falls. Here, only the sum of the source and sensor noises is acquired. The intensity of a pixel can rise randomly above that of its neighbours. These local maxima incurred due to noise should not be regarded as peaks because their cause does not lie in a measured spectral line and they occur in multiple measurement of a given sample at changing pixels of the low-line areas. Accordingly, a "safe" signal-to-noise ratio ("noise threshold") Rmax is to be determined or to be estimated, by which a pixel must project beyond its neighbours, in order for it to be assumed that a spectral line is present. The total noise RGes is composed of a sensor noise portion RSens and a source noise portion RQuelle. RSens can be estimated by a series of measurements being carried out with the excitation source switched off. Thereafter, the standard deviation of the measured values is determined pixel by pixel. The highest standard deviation of a pixel serves as an estimate of RSens upwards. The source noise is less critical for the classification of a local maximum as a peak. Although the pixel intensities of several sources, e.g. of the electrical arc, not rarely fluctuate by 20% from measurement to measurement, the quotient of adjacent pixels remains almost the same; in other words, adjacent pixels fluctuate "in rhythm". In order to be able to measure the remaining relative fluctuation of adjacent pixel intensities upwards, a measurement series with m measurements is again carried out on a sample rich in lines. Only pixels are considered which deliver intensities which are well over the sensor noise. For the remaining pixels Px, for each measurement i of the measurement series the quotient $QRPx_i$ is formed between the pixel intensity and the pixel intensity of the right-hand neighbour pixel. In this way, for elements Px of a part quantity of the sensor pixels a measurement range is obtained in each case of quotients $QRPx_i$ which consists of m elements. For each of these series the variation coefficient $V_{P_x}$ can now be determined. As long as neither the numerator nor the denominator pixel intensity of QRPx$_i$ reaches the saturation limit, $V_{P_x}$ is similar for pixel pairs and small (typically less than 1%). However, if one of the pixels moves into saturation, it will no longer act fully in sympathy with the source fluctuations, while its weaker intensity partner pixels can still do so. The result is an increased $V_{P_x}$. For this reason, it is a good approach also to exclude pixel pairs with which at least one pixel lies in the vicinity of the saturation limit. Let MaxV be the greatest of the remaining $V_{P_x}$. The value MaxV is a suitable estimate for the relative intensity difference Rquelle upwards, by which the local maximum must project above at least its neighbours (in the absence of any sensor noise) in order to be regarded as a peak.

Accordingly, for a pixel Px an estimated noise portion $RGes_{Pxi}$ is obtained, which is dependent on the intensity of the measured pixel:

$$RGes_{Px}=PSens+Mes[Px]*RQuelle \qquad \text{(Equation 4)}$$

In order to arrive at a noise threshold $Rmax_{Px}$, which with high statistical reliability will not be exceeded, $RGes_{Px}$ is multiplied by a factor f.

$$Rmax_{Px}=f*RGes_{Px} \qquad \text{(Equation 5)}$$

If normally distributed noise is eliminated, and if f=3 is selected, the actual noise will, to a degree of probability of more than 99.7%, lie below $Rmax_{Px}$.

Figure 10:
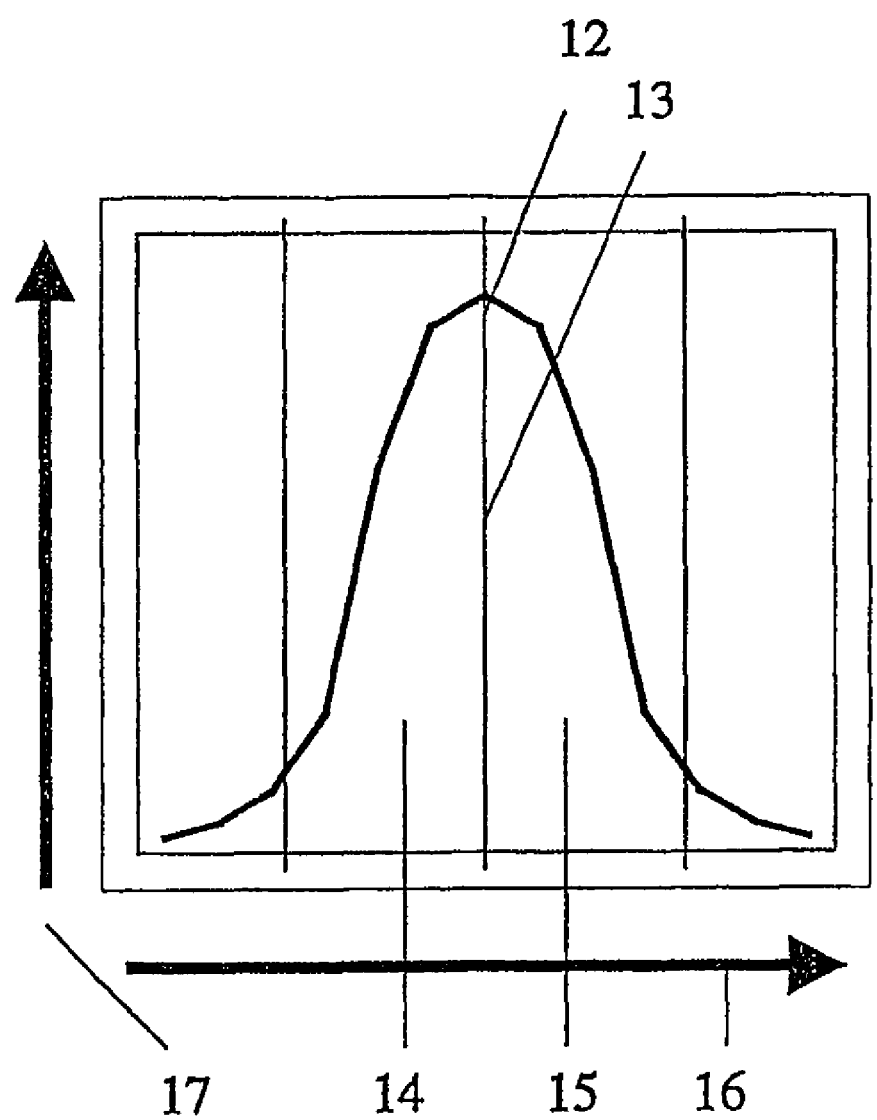
FIG. 10 shows a situation in which a radiation maximum of a spectral line falls exactly onto a boundary of two pixels.

One point of the spectrum must therefore be raised above its surroundings by $Rmax_{Px}$ in order for it to be said reliably that a peak is present at this point (a spectral line or an unresolved superimposition of several spectral lines). It is not a good approach, however, for the presence of a peak at Px to be required to fulfil the term $$MeS[Px-1]+Rmax_{Px}<Mes[Px] \wedge Mes[Px+1]+ Rmax_{Px}<Mes[Px] \qquad \text{(Equation 6)}$$

as a simple example shows. Represented in FIG. 10 is a situation in which the radiation maximum of a spectral line (12) falls exactly onto the boundary of two pixels (13). The pixel to the left of the maximum (14) and the pixel to the right of the maximum (15) both have the same intensity. Equation 6 can, regardless of Rmax, never be fulfilled. Even if the line maximum does not exactly impinge on the pixel boundary, the difference between the two peak pixel intensities can be smaller than $Rmax_{Px}$. A suitable procedure is to move from the peak maximum to the left (right) for as long as required until intensity differences of at least $Rmax_{Px}$ are found. If the pixels PxL and PxR found in this way on the left and right, both have a lower intensity than Px, a peak has been found. Algorithm 1 reproduces the method step described in a formalized manner.

```
Funktion IsPeak(Px,Mes) // Test, ob im Spektrum Mes bei Pixel Px ein hoher Peak liegt
    // f, RSens und RQuelle sind zuvor ermittelte Konstanten, siehe Text
    RMaxPx:=f*( RSens + Mes[Px]*RQuelle) ;
    PxL:=i-1;
    Solange | Mes[PxL]-Mes[Px]|<RMaxPx PxL :=PxL-1 Ende ;
    PxR:=i-1 ;
    Solange | Mes[PxR]-Mes[Px] |<RMaxPx PxR :=PxR-1   ;
    Resultat := (Mes[Px]>Mes[PxL])∧ (Mes[Px]>Mes[PxR])
```

Algorithm 1: Test for the Presence of a Peak with Pixel Px

With the control sample search, peaks of the control sample are compared with those of an unknown sample. The intention is to determine whether both spectra derive from samples which belong to the same control sample class. As has already been explained earlier, the concentrations for alloy elements may deviate from one another by a predetermined factor, e.g. 100% relative. It may now happen that a peak, for example in the spectrum of the unknown sample, lies above the noise level. In the control sample spectrum, however, the corresponding peak may possibly not project over the noise level any longer because of a low concentration. In order, nevertheless, to be able to make an unambiguous comparison, a function IsHiPeak is introduced. If the value true is derived, the peak at px rises so far out of the noise level that, even with half/double concentration of the analyte concerned, a peak will be recognised in the corresponding spectrum.

```
Funktion IsHiPeak(Px,Mes) // Test, ob im Spektrum Mes bei Pixel Px ein hoher Peak liegt
    // f, RSens und RQuelle sind zuvor ermittelte Konstanten, siehe Text
    // KAbwLPKlasse Konzentrationsabweichung innerhalb einer Leitprobenklasse, z.B. 2
    RMaxPx:=KAbwLPKlasse*f*( RSens + Mes[Px]*RQuelle) ;
    PxL:=i-1 ;
    Solange | Mes[PxL]-Mes[Px] |<RMaxPx PxL :=PxL-1 Ende ;
    PxR:=i-1;
    Solange | Mes[PxR]-Mes[Px] |<RMaxPx PxR :=PxR-1     ;
    Resultat := (Mes[Px]>Mes[PxL])∧ (Mes[Px]>Mes[PxR])
```

Algorithm 2: Test for Presence of a High Peak at Pixel Px

Determination of the Precise Location of the Peak Maximum

Figure 11:
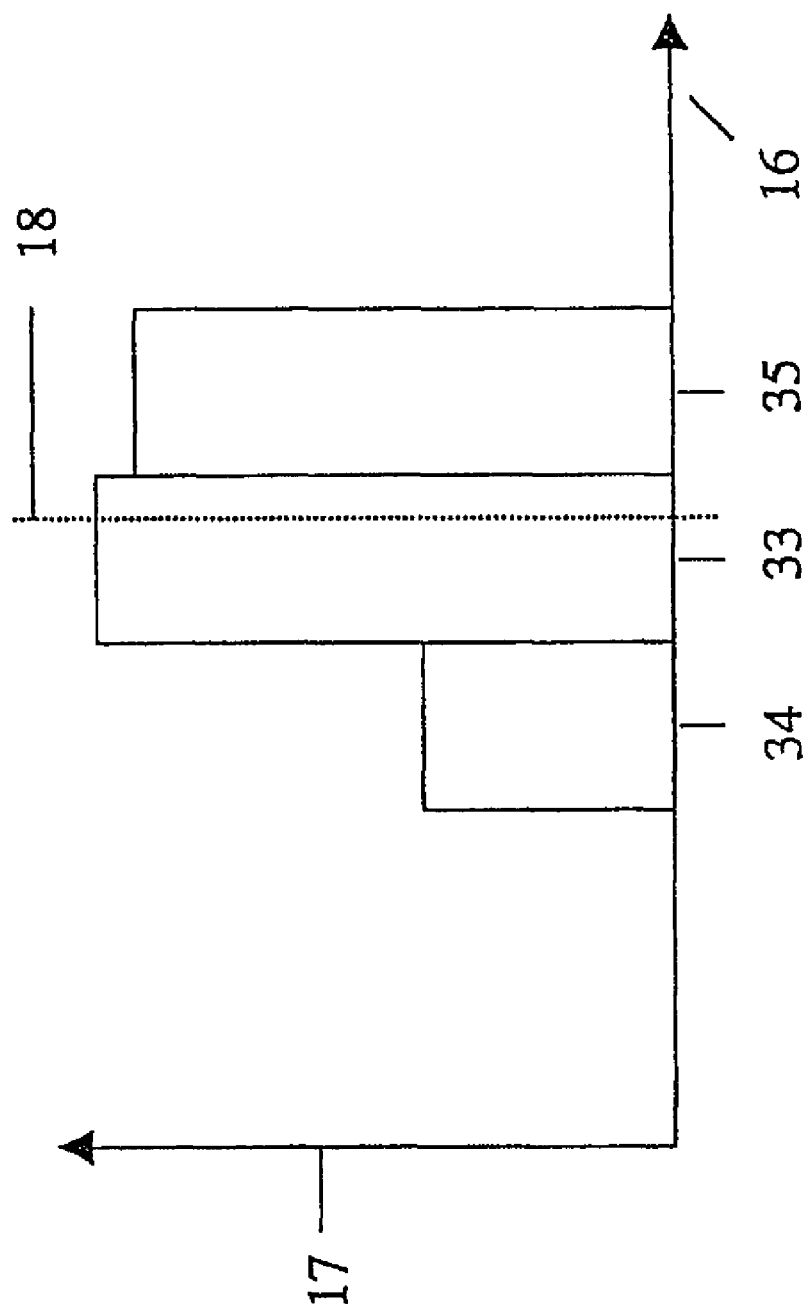
FIG. 11 shows bar charts of intensities of pixels.

In order to make a comparison of the peak intensities of the control sample spectrum and the spectrum of the unknown sample, as well as for drift checking and correction, the precise position of the peak maxima is required. In order to determine the position, the intensity of the peak maximum pixel (33) and the intensities of its left (34) and right (35) neighbour are required. In FIG. 11 these three intensities are reproduced as bar charts. It is now easy to determine the parallels (18) to the intensity axis, for which the same area lies to the left and the right. Algorithm 3 shows the calculation.

```
Funktion BestimmeMaximumPosition(Px,Mes)
// Genaue Maximumposition des Peaks bei Pixel Pxim Spektrum Mes bestimmen
    HalbeFläche      :=    (Mes[Px-1] +Mes[Px] + Mes[Px+1])/2 ;
    RestFläche       :=    HalbeFläche-Mes[Px-1] ;
    Resultat         :=    Px-0,5+RestFläche/Mes[Px];
```

Algorithm 3: Determination of the Position of the Peak Maximum

Spectra Comparison

It is now possible for an algorithm (Alg. 4) to be provided which determines the optimum control sample and determines any optics drift which may have occurred. The spectrum of the unknown sample is compared with each individual control sample spectrum. The comparison takes place peak by peak. In the first instance, all the peaks of the unknown sample are run through, then all the peaks of the control sample. If IsHiPeak is valid for the current peak and if, despite this, no peak is found in the comparison spectrum, an error numerator FehlerSumme is increased by one. If a corresponding line pair is found (line in the spectrum of unknown sample/line in the spectrum of the control sample are no more than MaxAbw pixels apart from one another), the position deviation is stored for the determination of the deviation frequency distribution. It should also be tested whether the intensity deviations are so great that the maximum tolerated relative concentration deviation for membership of a control sample group is exceeded. As already mentioned earlier, it has proved to be a good approach for concentration deviations of up to 100%) to be allowed within a control sample group. An intensity deviation of n % is in general based on a concentration deviation of more than n %. With an intensity deviation by a factor f, the error numerator will be increased by (f–1)/G but as a maximum by one. The limitation to 1 is a good approach, because two samples which have a spectral line at the same position are more similar even in the event of substantial intensity differences (with regard to the analyte which gives rise to the spectral line) than would be the case in the event of the complete absence of the line in one of the two spectra. The choice of the constant G is based on the assessable dynamic range. For CCD sensors, G=5 has proved its worth.

If a comparison between the spectrum of the unknown sample and a control sample ends with an error sum which is lower than the previous lowest MinFehler error, this control sample is stored as the candidate BesteLP. The drift which relates to this is written as a median of the position deviations into the variable Drift. For practical use it is recommended that the algorithm is further refined. Thus, for example, the variable BesterFehler can be checked. In the ideal case this is 1, then at each (high) peak of the unknown sample a control sample peak is located, and vice-versa. With a value of BesterFehier close to 1, the material class (control sample class) was unambiguously determined, and steps 3 to 10 of the method can be run through and the concentrations calculated accordingly.

However, if BesterFehler is substantially smaller than 1 (e.g. 0.9 or smaller), this is an indicator that a material was measured which cannot be allocated to any stored control sample.

```
Prozedur LPSuche
    BesterFehler:=MaxFloat // Größte darstellbare Gleitkommazahl
    Für alle Leitproben LeitProbe
        AnzPeaks:=0;
        AnzPaare:=0;
        FehlrSumme:=0;
        Von Px:=LR bis RR
            Wenn IsHiPk(Px,Mes)
                Bestimme Peakhöhe IdPkInt im Spektrum Mes
                PkPos:= BestimmeMaximumPosition(Px,Mes)
                Suche zu PkPos nächstgelegenen Peak mit Position LeitPkPos und Höhe LeitPkInt
                im Leitprobenspektrum Leit;
                AnzPeaks:=AnzPeaks+1
                Die Position dieses Leitproben-Peaks wird in LeitPkPos gespeichert;
                Abweichung:=PkPos-LeitPxPos;
                Wenn |Abweichung|<MaxAbw // Korrepondierendes Linienpaar gefunden
                    AnzPaare:=AnzPaare+1;
                    // Häufigkeitsverteilung Positionsabweichungen aufbauen
                    AbwMal10:=Gerundet(10*Abweichung)];
                    AbwKlasse[AbwMal10]:=AbwKlasse[AbwMal10]+1;
                    IntFehlr :=(Max(IdPxInt,MesPxInt)/Min(IdPxInt,MesPxInt)-1)/G
                    // G ist eine Konstante z.B. 5, siehe Text
                    Wenn IntFehler>1 IntFehler:=1 Ende;
                    FehlerSumme:=Fehlersummr+IntFehler;
                Sonst // Kein korrespondierendes Linienpaar gefunden
                    FehlerSumme:=Fehlersumme+1;
                Ende (des Wenn-Blocks)
            Ende (des Wenn-Blocks)
            Wenn IsHiPk(Px,Leit)
                Bestimme Peakhöhe LeitPkInt im Leitprobenspektrum Leit
                Suche zu PkPos nächstgelegenen Peak mit Position IdPkPos und Höhe IdPkInt
                im Spektrum Mes der zu identifizierenden Probe;
                AnzPeaks:=AnzPeaks+1;
                Die Position dieses Peaks wird in IdPkPos gespeichert;
                Abweichung:= PkPos-IdPxPos;
```

-continued

```
        Wenn Abweichung|<MaxAbw // Korrepondierendes Linienpaar gefunden
            AnzPaare:=AnzPaare+1;
            AbwMal10:=Gerundet(10*Abweichung)];
            AbwKlasse[AbwMal10]:=AbwKlasse[AbwMal10]+1;
            IntFehler :=(Max(IdPxInt,MesPxInt)/Min(IdPxInt,MesPxInt)-1)/G
            // G ist eine Konstante z.B. 5, siehe Text
            Wenn IntFehler>1 IntFehler:=1 Ende;
            FehlerSumme:=Fehlersumme+IntFehler;
         Sonst // Kein korrespondierendes Linienpaar gefunden
            FehlerSumme:=Fehlersumme+1;
         Ende (des Wenn-Blocks)
      Ende (des Wenn-Blocks)
   Ende (der Von-Schleife)
   Wenn FehlerSumme/AnzPeaks <BesterFehler
      // Bislang beste Leitprobe gefunden
      BesterFehler:= FehlerSumme/AnzPeaks; BesteLP:=LeitProbe;
      // Die Häufigkeitsverteilung der Positionsabweichungem steht (in Zehntelpixelabständen) in
AbwKlasse[ ]
      Summe:=0;
      Von Klasse := -MaxAbw*10 bis MaxAbw*10 // Drift wird Median der Häufigkeitsverteilung
         Summe:=Summe+AbwKlasse[Drift];
         Wenn Summe<AnzPaare/2 Drift:=Klasse Ende (Wenn);
      Ende (Von Klasse := -MaxAbw*10 bis MaxAbe*10)
   Ende (Wenn FehlerSumme/AnzPeaks <BesterFehler)
Ende (der Für alle Leitproben LeitProbe)
Ende ( der Prozedur LPSuche)
```

Algorithm 4: Control Sample Search

REFERENCE NUMBER LIST

1. Stand
2. Sample
3. Counter-electrode
4. Excitation generator
5. Optical system
6. Focal curve
7. Source slit
8. Concave grating
9. Exit slit
10. Photo multiplier tubes
11. Multi-channel sensors
12. Radiation maximum of a spectral line
13. Pixel boundary
14. Pixel left of the maximum
15. Pixel right of the maximum
16. Pixel axis
17. Intensity axis
18. Parallels to intensity axis
19. Spectrum of alloy 2.4375 at 329 nm
20. Spectrum of alloy 2.4634 at 329 nm
21. Spectrum of alloy Nl 200 at 329 nm
22. Spectrum of a sample of material 1.4404 at 471.4 nm
23. Spectrum of a sample of material 1.4401 at 471.4 nm
24. Intensity change of the Ni line 388.98 at arc current change
25. Intensity change of the Ni line 397.22 at arc current change
26. Axis for "arc current in Amperes"
27. Axis for "relative intensity relating to intensity at 1.5 A arc current"
28. Intensity change of the Cr line 385.42 nm at arc current change
29. Intensity change of the Ni line 397.13 nm at arc current change
30. Axis for "Intensity ratios normed to intensity ratios at 1.5 A arc current"
31. Intensity ratios Cr 385.42 nm/Ni 388.98 nm
32. Intensity ratios Cr 397.13 nm/Ni 397.22 nm
33. Intensity of the maximum pixel
34. Intensity of the left neighbour of the maximum pixel
35. Intensity of the right neighbour of the maximum pixel
36. Intensity change of Ni 397.22 nm at arc current change, Ni 200
37. Intensity change of Ni 388.98 nm at arc current change, Ni 200

The invention claimed is:

1. Method for the spectral analysis of metal samples, the method comprising:
    a. recording of a spectrum of an unknown sample with a number of preset excitation parameters, at least one of which is independent of a control sample,
    b. comparison of the spectrum with stored spectra of a number of control samples,
    c. determination of the control sample with the best spectral concordance with the spectrum of the unknown sample of spectra,
    d. setting of the excitation parameters, which are stored for the best and closest control sample determined in step c,
    e. recording of the spectrum of the unknown sample with the excitation parameters set in step d, and
    f. calculating the intensity ratios of the analysis lines stored for the control sample and the internal standards of the spectrum recorded in step e.

2. The method according to claim 1, wherein in step a., a fixed predetermined arc current from 1.5 to 2.8 Amperes is used.

3. The method according claim 1, wherein in step b. the number of deviations between the lines in the sample spectrum and the control sample spectra is determined for each control sample, and in that step c., that the control sample is selected with the lowest number of deviations.

4. The method according to claim 1, wherein the following additional step is provided:
    determining a concentration ratio of alloy element El in accordance with the formula:

$$KV_{El} = KV_{Leit} + E^*(1 - Int_{El}/Int_{Leit}),$$

wherein $KV_{El}$ represents a concentration ratio of allo element El in the unknown sample, E represents a sensitivity factor, $KV_{Leit}$ represents a concentration ratio of alloy element El in the control sample determined in step c., $Int_{El}$ represents an intensity ratio for a line pair used for alloy element El, as measured based on the unknown sample, and $Int_{El}$ represents an intensity ratio for a line pair used for alloy element El, associated with the control sample determined in step c.

5. The method according to claim 1, wherein the following additional step is provided:

calculating a concentration $K_{El}$ for an element El of a total of n elements based on concentration ratios, according to the equation:

$$K_{E1} = \frac{KV_{E1}}{\left(100 + \sum_{i=1}^{n} KV_{i,U}\right)},$$

wherein $KV_{El}$ represents a concentration ratio of element El in the unknown sample and $KV_{I,U}$ represents a concentration ratio of an $i^{th}$ element in the unknown sample.

6. The method according claim 1, wherein the following additional step is provided:

providing element concentrations in a selection and sequence stored with the control sample.

7. The method according claim 1, wherein the following additional step is provided for:

conducting element concentrations to routine for identification.

8. A device for the spectral analysis of metal samples by means of optical emission, comprising:

an excitation source, which operates on the principle of electrical excitation;

at least one optical system for the splitting of the optical emission in spectral lines;

a number of location resolving detectors;

a control device for the sequence of the spectral analysis; and a memory for storing a plurality of control sample data records, wherein one control sample data record comprises at least one part of a control sample spectrum and excitation parameters provided for this control sample;

wherein the control device is arranged to automatically set the excitation parameters to be used in analyzing a metal sample; and wherein the control device is further arranged, in a first analysis, to set an excitation parameter independent of a control sample, in order to carry out a first spectral analysis, to compare the result with the control sample data records, and then to set the excitation parameters which have been stored for a next control sample coming.

9. The device according to claim 8, wherein the excitation source is an arc excitation source.

10. The device according to claim 8, wherein the excitation parameters comprise at least a current.

11. The device according claim 8, wherein the control sample data records comprise information about suitable spectral lines for the spectral analysis of each individual control sample.

12. The device according to claim 8, wherein the control is further arranged to set an excitation parameter to a preset value for the measurement of a spectrum of an unknown sample; to compare the spectrum of the unknown sample with one or more of the stored control sample spectra; and to select the excitation parameter corresponding to a control sample spectra most closely matching the spectrum of the unknown sample.

13. The device according to claim 12, wherein the control unit is further arranged to set the excitation parameter to the selected excitation parameter for a further measurement of the spectrum of the unknown sample.

* * * * *